United States Patent [19]

Hussein et al.

[11] Patent Number: 4,646,737

[45] Date of Patent: Mar. 3, 1987

[54] LOCALIZED HEAT APPLYING MEDICAL DEVICE

[75] Inventors: Hany M. G. Hussein, Lindenhurst; Marvin P. Loeb, Chicago, both of Ill.

[73] Assignee: Laserscope, Inc., Santa Ana, Calif.

[21] Appl. No.: 503,783

[22] Filed: Jun. 13, 1983

[51] Int. Cl.$^4$ .............................................. A61B 17/36
[52] U.S. Cl. ........................... 128/303.1; 219/121 LZ
[58] Field of Search ..................... 128/303.1, 395–398, 128/401, 303.17; 219/121 LZ

[56] References Cited

U.S. PATENT DOCUMENTS

| | | | |
|---|---|---|---|
| 3,136,310 | 6/1964 | Meltzer | 128/398 X |
| 4,074,718 | 2/1978 | Morrison, Jr. | 128/303.17 |
| 4,209,017 | 6/1980 | Shaw | 128/303.1 |
| 4,233,493 | 11/1980 | Nath | 128/398 |
| 4,266,549 | 5/1981 | Kimura | 128/303.1 |
| 4,423,726 | 1/1984 | Imagawa et al. | 128/395 |
| 4,437,474 | 3/1984 | Peers-Traverton | 128/784 |
| 4,445,892 | 5/1984 | Hussein et al. | 128/303.1 X |
| 4,448,188 | 5/1984 | Loeb | 128/395 X |
| 4,449,528 | 5/1984 | Auth et al. | 128/303.1 |

FOREIGN PATENT DOCUMENTS

| | | | |
|---|---|---|---|
| 2826383 | 12/1979 | Fed. Rep. of Germany | 128/303.1 |
| 2829516 | 1/1980 | Fed. Rep. of Germany | 128/303.1 |
| 2832847 | 2/1980 | Fed. Rep. of Germany | 128/303.1 |

OTHER PUBLICATIONS

Protell et al., "The Hecter Probe . . . ", Gastroenterology, 74:257-262, 1978.

Primary Examiner—Lee S. Cohen

[57] ABSTRACT

A medical device for applying localized heat to a portion of a patient's body is disclosed. Generally, the device includes a light transmitting conduit and a heat generating element which converts transmitted light into heat. A suitable exterior tube can also be provided for guidance, strength and delivery of fluids. The medical device can be used to cauterize or destroy tissue, or alter or remove deposits from lumens. The medical device can also serve as part of a system which provides the light and measures the temperature of the element.

59 Claims, 8 Drawing Figures

LOCALIZED HEAT APPLYING MEDICAL DEVICE

TECHNICAL FIELD OF THE INVENTION

This invention relates to medical devices and procedures for applying localized heat to a site in a patient's body for such purposes as removing tissue or deposits or cauterizing tissue.

BACKGROUND OF THE INVENTION

Providing localized heat to a site in a patient's body has often been used to cauterize a lesion to stop bleeding. Localized heat can also be used to alter, remove, or destroy tissue in a patient's body. One example of such localized heating is the treatment of a bleeding ulcer. An endoscope is inserted through a patient's esophagus to view the bleeding site and direct an electric powered heating element to contact the site and cauterize the bleeding. Another example is the use of such heat to remove neoplastic pulmonary tissue.

Unfortunately, electric heating elements can be difficult to manipulate and generally heat up relatively slowly. The heating rate and maximum sustainable temperature is limited by the electric current available to the element. The available current in turn is limited by the size of the wires leading to the element. Wire size limits access to body sites for two reasons: larger wires cannot be inserted into small areas and increased wire size also means a loss of flexibility.

The electric current passing through the wires also limits the regions in the body in which such a device can be used. There is the threat of an electric shock to the patient and the generated electric field about the wires by flowing current can also have undesirable effects. One region where such electric currents and fields could possibly be life threatening is in the heart.

One proposal which heats the end of an endscope to avoid dew forming on a window is shown in U.S. Pat. No. 4,279,246 to Chikama. That device heats the window to about body temperature to prevent dew formation. However, due to the design of the device, the heat generated on the window is limited to about body temperature and therefore could not be used to alter or destroy tissue.

Cardiovascular disease continues to be an ongoing problem, particularly in complex societies. It has been estimated that every year more than one-half million Americans die from cardiovascular disease. Another 3.5 million are believed to suffer some degree of incapacitation because of this disease. A particularly serious problem is the progressive blockage of a blood vessel by the collection or deposit of fatty material such as arteriosclerotic plaque. The collected material at first constricts the vessel, reducing blood flow to a relatively small channel. Eventually, blood flow can be obstructed completely.

Various devices and methods have been proposed in an attempt to deal with obstructed or constricted blood vessels. In one method, a balloon is positioned within the constricted channel and inflated, compressing the plaque into the vessel walls to widen the opening. This method is only available when the constriction in the blood vessel is not so severe that the remaining channel is too small for the deflated balloon. Compression of the plaque into the vessel walls is not possible where the plaque has become calcified and hard. Such a method is not even attempted in completely obstructed vessels.

Accordingly, it would be desirable to provide a method and device which avoids the shortcomings of the prior art yet provides an effective means for delivering localized heat to a site within a patient's body. The heat provided by such a device can be used to stop bleeding or remove body tissue or material in a blood vessel, even a completely obstructed blood vessel. For such a device, the heat should be quickly developed without use of electrical current. Also, the device should be sufficiently small so that it can be directed into a patient's body cavity or lumen such as a blood vessel. It would also be desirable to provide rapid and accurate measurement of the heat produced. The present invention meets these desires.

SUMMARY OF THE INVENTION

The present invention contemplates a medical device, system and method for applying localized heat to a site in a patient's body. The localized heat provided in accordance with the present invention can be used for several purposes such as cauterizing a lesion to stop bleeding, or to remove a clot, or to remove an arteriosclerotic deposit from a blood vessel. The heat available can also be used to create an open channel in a previously occluded blood vessel.

Generally, the medical device embodying this invention includes a heat generating element mounted on the distal end of an elongated light transmitting conduit. A preferred conduit is a single flexible quartz optical fiber. Light energy from an intense light source such as a laser is transmitted through the conduit and emitted onto a light receiving surface of the heat generating element. The light is converted by the element to generate heat. The element can then be contacted with a material in a patient's body such as a clot, deposit or tissue to alter that material by melting, removing or destroying it. The heat generating element preferably has a rounded exterior surface end and is retained on the conduit by a locking means, such as a ridge on the element received in a complementary groove on the conduit.

Since light is used to transfer energy to the heat generating element, there are no electrical currents present which could possibly threaten the patient. Also, far more energy can be conducted by light through an optical fiber than by electricity through wires of the same diameter. The use of an intense light from a laser allows a substantial amount of energy to be rapidly transferred to the heat generating element for rapid heating. This avoids the difficulties inherent in electrical systems, including the presence of electrical currents and the relatively slow heating of the element.

The medical device can be used as part of a system which also includes a light source for providing sufficient light energy to raise the temperature of the element to soften the deposit in a blood vessel, and temperature sensing means associated with the light transmitting conduit for monitoring the temperature of the element. The preferred light source is a laser and the preferred temperature sensing means is a pyrometer. Other such means can be utilized, however. The laser is activated to transmit an intense light pulse through the conduit. The light is emitted by the conduit onto the receiving surface of the heat generating element which converts the light energy into heat. After the laser is deactivated, the light or glow from the hot element is transmitted back through the light transmitting conduit.

This glow is then converted by the pyrometer into a temperature reading or measurement.

The medical device can also be provided with an elongated tube which carries the light transmitting conduit. The heat generating element extends beyond the distal portion of the tube so it may be brought into contact with the tissue or deposit to be heated. The tube helps guide the conduit to the desired location and is particularly useful for providing access to a blood vessel. The exterior of the tube can be provided with blood flow occlusion means such as an inflatable balloon to selectively stop the flow of blood. A fluid such as saline, a radiopaque liquid or carbon dioxide can also be introduced through a passageway defined by the tube.

A viewing system to permit viewing within the lumen or blood vessel can also be provided as part of the medical device. Generally, the viewing system includes a fiberoptic viewing bundle carried by the tube to provide a view of the heat generating element and the tissue or obstruction about to be contacted. A suitable clear flushing fluid can be introduced through the passageway defined by the tube to provide improved viewing.

In use, the medical device is inserted into a patient's body such as by positioning the distal end of the medical device within a blood vessel. The element is contacted with a site such as a constriction, and light energy is transmitted through the conduit to heat the element rapidly and sufficiently to soften and open at least a portion of the constriction as the element contacts the constriction and is urged forward. In one preferred method aspect, the blood flow is occluded by the balloon and a radiopaque liquid introduced into the vessel to allow fluoroscopic study of the constriction and location of the medical device. It is particularly preferred also to introduce a bubble of biologically compatible gas such as carbon dioxide into the vessel about the element prior to the light transmission. This avoids dissipation of heat into the liquid or blood otherwise in contact with the element.

Numerous other advantages and features of the present invention will be readily apparent to those skilled in the art from the following detailed description of the preferred embodiments of the invention, the drawings, and the appended claims.

DESCRIPTION OF THE PREFERRED EMBODIMENTS

While this invention can be embodied in many different forms, there are shown in the drawings and described in detail, preferred embodiments of the invention. The present disclosure is an exemplification of the principles of the invention and is not intended to limit the invention to the embodiments illustrated.

The present invention is a medical device for delivering and applying localized heat to a site in a patient's body. The heat can be used to stop bleeding or remove or alter a material such as tissue or deposit in the body. The material being altered can be any solid or semi-solid substance found in the body including living tissue or deposits such as clots, fat or arteriosclerotic plaque.

Figures 1, 2, 3:
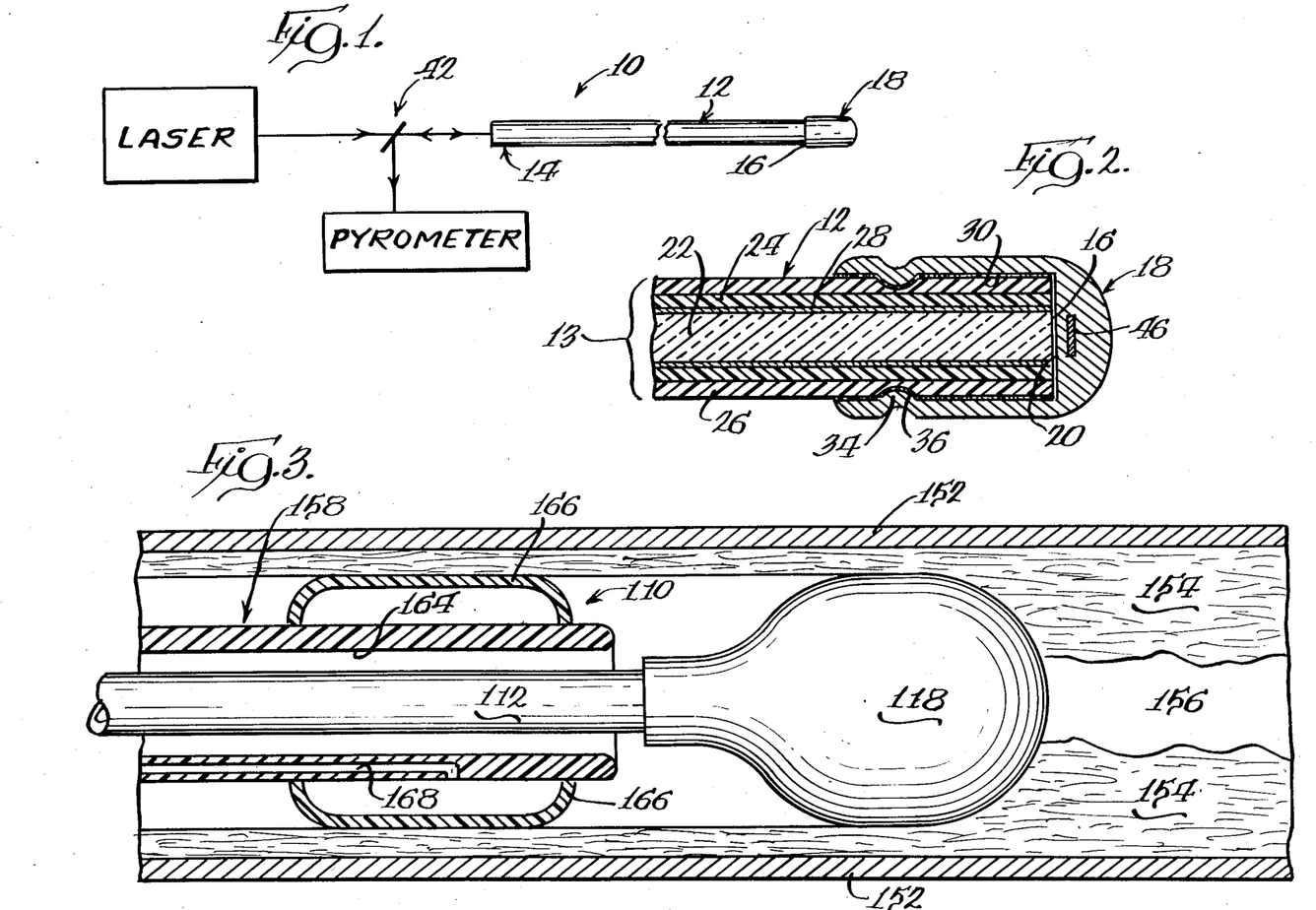
FIG. 1 is a schematic view of a system including a medical device embodying the present invention.
FIG. 2 is an enlarged cross-sectional elevational view of the distal end portion of the medical device of FIG. 1.
FIG. 3 is another enlarged elevational view, partly in section, of a further alternative embodiment of the medical device shown received within a blood vessel having a constriction.

FIGS. 1 and 2 show a medical device 10 embodying the present invention and including an elongated light transmitting conduit 12 such as an optical fiber or a microwave channel or waveguide, having a proximal end 14 and a distal end 16. A heat generating element 18 is mounted with respect to the distal end 16 of the conduit 12 such that light transmitted by the fiber is absorbed and converted by the element into heat. The light is emitted by the distal end 16 of the conduit and is received and collected by a light receiving surface 20 on the element 18. The element 18 is preferably mounted on the distal end 16 of the conduit 12 and retained in that position by appropriate means discussed in more detail below. Mounting the element 18 directly on the conduit 12 insures that the light is properly delivered and the element will not become disengaged from the conduit.

The conduit 12 is preferably a single, flexible light-transmitting fiber such as used in fiberoptic devices and generally has a total exterior diameter of about one millimeter or less. A single fiber generally has the rigidity needed to press the element into a deposit or tissue. Larger or smaller fibers can be used depending on the available area in a patient. Generally, the single, light-transmitting fiber 13 includes a fiber core 22 surrounded by cladding 28. The internal reflection caused by the cladding 28 should be such that the fiber 13 has a low divergence as the light exits the distal end 16. The core 22 and the cladding 28 are made of glass, e.g. silica quartz with a combined diameter of less than about 0.5 millimeter to about 1.0 millimeter. Substantially all of the light exiting the distal end 16 should be directed forward to be absorbed by the light receiving surface 20. This generates the majority of the heat at the forward end of the heat generating element 18 where it is needed while minimizing the heat on the rearward portions of the element where it could otherwise be detrimental to the fiber 13.

To protect the fiber core 22 and cladding 28, the fiber also includes a jacket 26 which surrounds the cladding 28 and is held in place by a resin coating 24. The external jacket 26 is usually made of a flexible plastic material such as poly(ethylene) or poly(tetrafluoroethylene). This also provides a flexible and smooth surface allowing easy manipulation of the medical device. Fiber optic bundles are not prefered since the glue between individual fibers limits the amount of light which can be transmitted without melting of the bundle.

The conduit 12 should be flexible yet sufficiently resilient so that it is possible to push the conduit along a lumen to drive the heat generating element 18 into and through an obstruction. One such suitable conduit is a fiber optic having a core diameter of 0.4 millimeters which is marketed under the trademark Med 400 by Quartz Products Corporation of Plainfield, N.J.

The forward portion of the heat generating element 18 is preferably generally rounded on its exterior surface to facilitate pressing the element into and through softened body material. The heat generating element can alternatively have other shapes as desired including oblong or eccentric with respect to the axis of the fiber or even generally crescent-shaped. Such an eccentric or oblong shape can be rotated to generate an even larger channel through an obstruction. A crescent-shaped element allows for fluid flow and viewing past the element.

The element 18 is preferably made of metal such as surgical stainless steel, but could also be made of a combination of thermally conductive and insulating material such as metal and ceramic. The inside light receiving surface 20 is preferably treated, e.g., oxidized, to increase its coefficient of emissivity to about 0.95 or greater to further increase the absorption of light by the element 18. Alternatively, the surface 20 can be treated by being coated by a material having a high coefficient of emissivity such as lamp or carbon black. The exterior surface of the heat generating element 18 is preferably coated with a non-stick or release surface such as poly(tetrafluoroethylene) to provide easy release from the tissue poly(tetrafluoroethylene) should only be used for operating temperatures below about 300 degrees C.

The distal end 16 of the conduit 12 is preferably positioned or received in cavity 30 defined by the rear portion of the heat generating element 18. The element 18 can be retained on the distal end 16 by appropriate means for mounting such as an adhesive, an appropriate locking means, or a combination of both. The locking means is preferably at least one inwardly extending, peripheral ridge 34 on the element 18 received in a complimentary groove 36 defined by the conduit 12. The groove 36 should extend into the jacket 26 but not into either the core 22 or the cladding 28. The adhesive such as hardened epoxy resin can be used to retain the element 18 on the conduit 12 while the ridges 34 are crimped into the groove. Since some adhesives may become ineffective under intense heat, the locking means provides a backup to ensure the element remains in place.

The heat generating element 18 has sufficient mass to avoid burn-through during use. However, the mass is not so great as to materially slow its heating rate. For this reason, it is advantageous to place the thickest portion of material in the forward portion of the element 18 where the light infringes. A minimum amount of space between the distal end 16 of the fiber and the light receiving surface 20 of the element 18 reduces the presence of other matter such as air or liquid which, if present in excess may require venting due to expansion as a result of the heat generated. Where such a space is provided, one or more vents are supplied to provide communication between the space and the outside surface of the element to the ambient surroundings.

The distal end 16 of the fiber is preferably spaced no more than 2 diameters of the core 22 away from the light receiving surface 20. Where the core is about 0.5 millimeters, this spacing should be no more than about 1 millimeter. This relatively close spacing insures that substantially all of the light is received on the forward light receiving surface 20 and is not dispersed on the inside side walls of the cavity 30.

The medical device can serve as part of a system which, as shown in FIG. 1, includes a light source such as a laser associated with the proximal end 14 of the fiber 13. The light source is chosen to deliver sufficient light energy to raise the temperature of the element 18 to soften material causing an obstruction or to destroy tissue. The system further includes temperature sensing means such as a pyrometer also associated with the proximal end 14 of the fiber for measuring the temperature of the element 18. Both the light source and temperature sensing means can be associated with the proximal end 14 of the fiber 13 by a beam splitting means 42. The beam splitting means 42 can be a partial mirror or a system such as a rotating or movable mirror. When the mirror is in a first position the laser light is directed into the fiber 13. After the laser is deactivated, the mirror is then placed in a second position to direct the resulting radiation or glow of the element 18 emitted by the fiber proximal end 14 to the pyrometer.

The laser produces the light which is converted by the heat generating element 18 into heat. The word light is used in its broad sense, meaning electromagnetic radiation which propagates through space and includes not only visible light, but also infrared, ultraviolet and microwave radiation. The laser is preferably used intermittently with temperature measurements made between uses. By monitoring the glow of the heated element 18 it is also possible to provide an advance warning of approaching burn-through where the element 18 has been provided with a layer of different metallic or non-metallic material 46 embedded within the forward portion of the element 18.

The light can enter the fiber continuously or intermittently, as desired, to maintain the element 18 above a predetermined temperature such that it is capable of softening a plaque deposit or cauterizing bleeding tissue. Where the medical device is used in a blood vessel, rapid heating of the element 18 is preferred since this allows the softening and removal of obstructing material while minimizing the amount of heat transferred to the tissues surrounding the blood vessel. A slower heating rate releases a greater total amount of energy into the entire tissue area while a rapid heating rate releases less total energy, but concentrates it in a small area within the material to be softened and removed. The element can be first heated i.e., light transmission begun, and then contacted with the deposit. This minimizes heat dissipation into the surrounding tissue and allows the element to reach a higher temperature before contact.

An alternative embodiment for the medical device 110 is shown in FIG. 3. The medical device is shown received within a blood vessel 152 having a deposit 154 which reduces the operative size of the blood vessel to a relatively small constricted channel 156. The medical device 110 includes a light transmitting conduit 112 and a heat generating element 118 substantially as described above. The element 118 includes an enlarged head portion to create a channel of relatively larger diameter in the deposit 154.

The medical device 110 also includes an elongated tube 158 having a proximal portion (not shown) and a distal portion 162 and defining a passageway 164 along its length. The elongated tube 158 allows for positioning the light transmitting conduit 112 and heated element 118 in a lumen such as blood vessel 152 by passing the tube through the skin and muscle layers of the patient into the blood vessel. The conduit 112 is slidingly received in the tube 158 so that it can be moved longitudinally with respect to the tube and the element 118 extended beyond the distal portion 162 of the tube. The element can be of such size that it may be received within the passageway 164 during the placement of the device within the blood vessel 152. The tube 158 is then first located in a vessel and a conduit 112 with a relatively small heated element as shown in FIG. 2 inserted into the tube 158.

Alternatively, the element 118 as shown in FIG. 3 can be relatively larger in cross section than the passageway 164 to create a larger channel in an obstruction. The heated element can even be larger than the outer diameter of the tube 158 allowing the tube to be advanced progressively as the element is repeatedly pressed forward to create a longer channel. When the heated element is larger in cross section than the passageway 164, the element can rest against the opening of the tube distal portion 162 during insertion into the blood vessel.

The defined annular passageway 164 permits the introduction of fluid into the blood vessel such as a radiopaque liquid which allows fluoroscopic study of the size and location of the deposit 154 and the constricted channel 156. The element 118, also radiopaque can also be fluoroscopically tracked. The conduit 112 and tube 158 can also be provided with radiopaque markings along their lengths for fluoroscopic tracking.

The tube 158 preferably carries a blood flow occlusion means such as an inflatable balloon 166 positioned circumferentially about the tube on the distal portion 162. The balloon 166 is preferably made of a suitable flexible plastic material and is inflated to contact and seal with the blood vessel wall by introducing a fluid such as carbon dioxide through a channel 168 defined by a thickened wall of the tube 158. After the blood vessel 152 has been occluded, a fluid such as a physiologically tolerable flushing liquid can be introduced through passageway 164. Suitable liquids include a saline solution, a dextrose solution, or an oxygen bearing liquid which provides oxygen to tissue downstream of the balloon. A radiopaque liquid can also be introduced for fluoroscopic viewing as described above. A physiologically tolerable gas such as carbon dioxide can also be introduced through the passageway 164 such that it surrounds the element 118 with a temporary gas bubble to minimize dissipation of heat from the element which otherwise would be directed into blood or radiopaque liquid. This also avoids damage to the blood. The gas bubble or introduced liquid can be withdrawn by suction through the passageway 164 after the procedure is over. Any debris generated can also be removed by suction.

Figure 4:
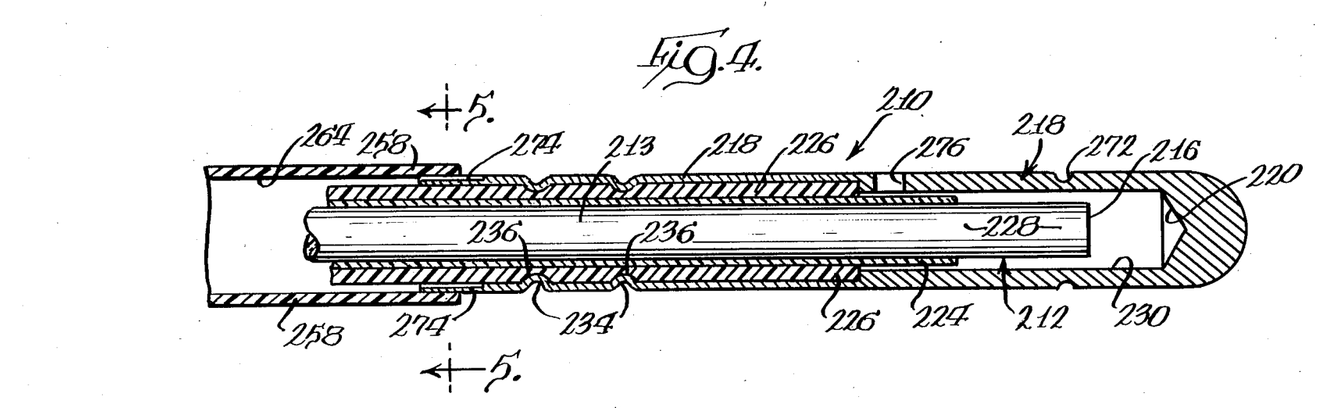
FIG. 4 is an enlarged elevational view, partly in section, of the distal end portion of a further alternative embodiment for the medical device.
Figure 5:
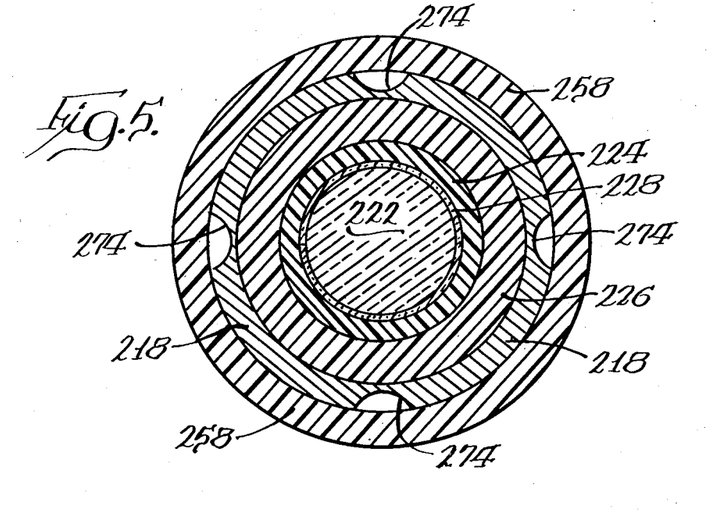
FIG. 5 is further enlarged cross-sectional view taken generally along plane 5—5 of FIG. 4 showing the internal structure of the medical device of FIG. 4.

A still further alternative embodiment for the medical device 210 is shown in FIGS. 4 and 5. As before, the heat generating element 218 is mounted on the distal end 216 of the light transmitting conduit 212. The resin coating 224 and jacket 226 have been trimmed back from the distal end 216 of the fiber 213 leaving a section of the clading 228 surrounding the fiber core 222 open to the sides.

The removal of the resin coating 224 and jacket 226 from the end portion of the fiber core 222 creates a spacing between the fiber core 222 and the element 218. The air in this space serves as an insulator between the element 218 and the fiber 213. Suitable other insulating materials can also be located between the element and fiber. Directing substantially all of the emitted light onto the light receiving surface 220 on the forward portion of the element 218 together with this spacing minimizes the conduction of heat from the element 218 to the jacket 226 of the conduit 212. To further limit the transfer of heat from the forward portion of the element 218 toward the rearward portion, a section of reduced metal thickness such as caused by a peripheral notch 272 can be provided. Because there is less metal in the area of the notch 272, a lesser cross-sectional area for heat conduction is available and there is less transfer of heat per unit time toward the rearward portion of the element 218.

The heat generating element 218 is retained on the conduit 212 by one or more inwardly extending ridges 234 received within corresponding peripheral grooves 236 in the jacket 226. The distal portion 262 of tube 258 engages the rear portion of the heat generating element 218 also to help retain the element on the conduit 212. The tube 258 can be made of the same material as the jacket 226, and is preferably a heat resisting plastic such as poly(tetrafluoroethylene). The tube 258 defines passageway 264 along its length through which the light transmitting conduit 212 is received.

The rear portion of the heat generating element 218 preferably defines at least one, and optimally a plurality of flutes 274 which are in fluid communication with the tube passageway 264. The flutes 274, together with the distal portion 262 of the tube, define openings through which a fluid such as carbon dioxide may be introduced through the passageway about the rear portion of the heat generating element 218. The introduced fluid is not only useful for clearing or removing debris produced about the heat generating element 218 when in use, but also helps to cool the rear portion of the element 218.

The elongated structure of the heat generating element 218 assists manipulation of the device 210 as when it is passed through a channel defined by an endoscope. To remove any gaseous material which may be generated within the cavity 230 defined by the heat generating element 218, a vent 276 can be provided on the side of the element in communication with the cavity 230.

Figures 6, 7, 8:
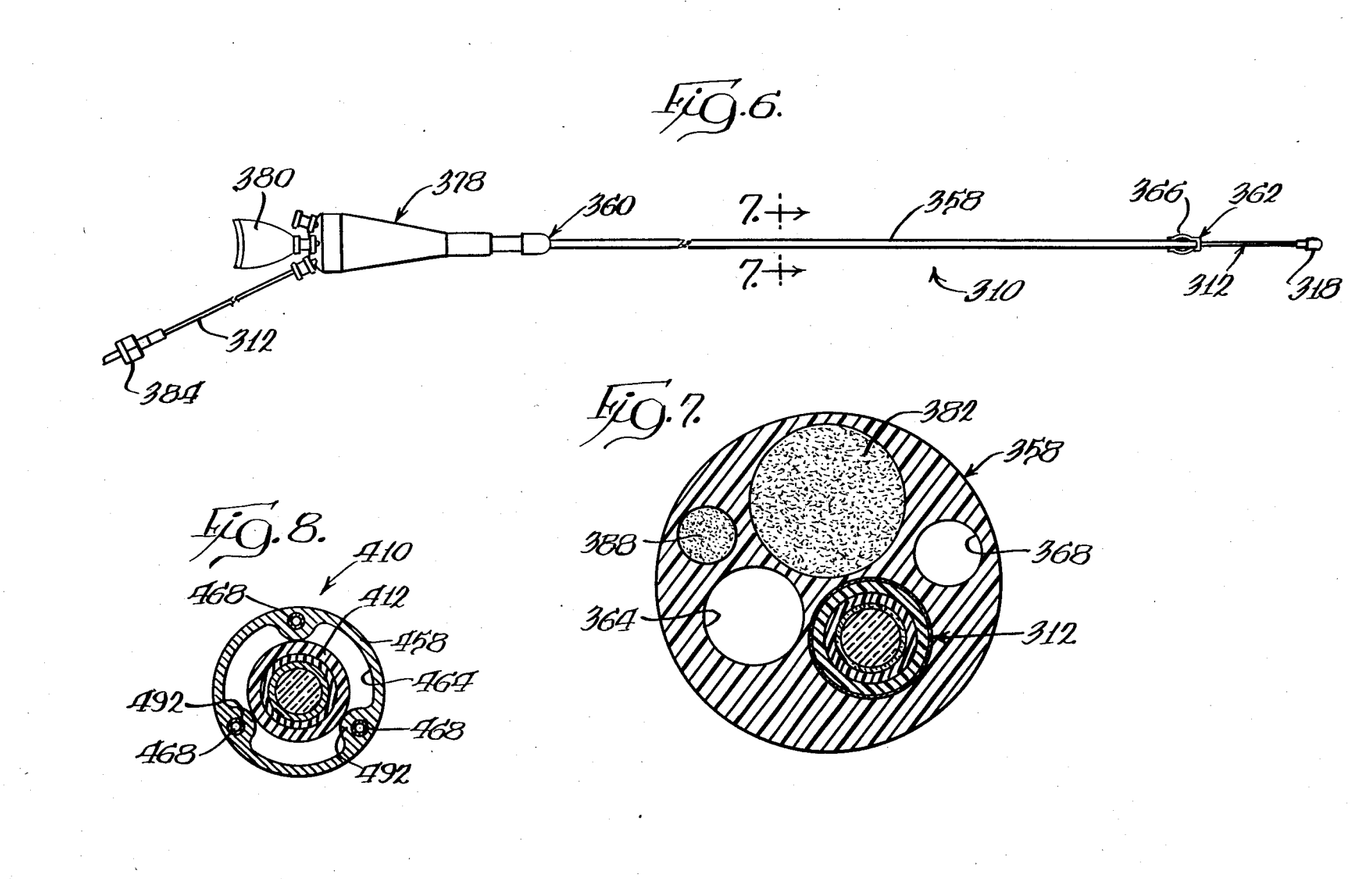
FIG. 6 is an elevational view of a further alternative embodiment for the medical device.
FIG. 7 is an enlarged cross-sectional view taken generally along plane 7—7 of FIG. 6 showing the internal structure of the medical device of FIG. 6.
FIG. 8 is a cross-sectional view of a still further embodiment for the medical device.

A still further embodiment for the medical device 310 is shown in FIGS. 6 and 7. In this embodiment, the medical device includes a heat generating element 318 mounted on the end of a light transmitting conduit 312 which is slidably received within an elongated tube 358. An inflatable balloon 366 is also included on the distal portion 362 of the tube 358. Mounted on the proximal portion 360 of the tube is an assembly including an eyepiece 380 that forms part of a viewing system. The viewing system also includes a fiberoptic viewing conduit 382 and illumination conduit 388 carried by the tube 358 together with the appropriate lens devices well-known in the art carried both by the assembly 378 and the distal end 362 of the tube.

The conduit 312 is slidably carried by the tube 358 and includes a connector 384 on its proximal end for linking with appropriate laser. The tube 358 also defines a channel 368 for inflating the balloon 366 and a flushing or suction passageway 364 for introducing fluids into a lumen. The passageway 364 can also be used in conjunction with a guide wire to direct the device into the patient.

In use, the distal portion of the medical device is inserted into a patient and positioned in the approximate desired location. The balloon 366 is then inflated to occlude the blood vessel. A clear fluid such as carbon dioxide or a liquid can then be introduced through the passageway 364 to allow viewing through the viewing system. Appropriate means can also be provided to wash the distal end of the viewing system. This allows visualization of the occlusion to be made prior to contact with the heat generating element 318 and also to determine the size of the size of the channel which has been opened by the heat generating element after it has been withdrawn.

As still further embodiment for the medical device 410 is shown in FIG. 8. The light transmitting conduit 412 extends through the elongated tube 458 and is centered within the defined passageway 464 along the central axis of the tube by centering means such as three longitudinal ridges 492 extending inward from the tube wall. Each ridge 492 preferably defines a channel 468 which can be used to inflate a balloon on the tube or for introduction of fluid through the distal end of the tube. The ridges 492 can be extrusion molded unitary with the remainder of the tube 458.

The ridges 492 center the conduit 412 and the element mounted on its distal end so that the element can be directed into the center of a lumen and avoid the lumen walls. The ridges 492 also minimize heat transfer from the conduit 412 to the tube 458 and hence to the lumen. The flow of a fluid through the passageway 464 about the conduit 412 also lowers its temperature during use.

The preferred lasers are Argon and Neodyminum-YAG. Tests were done with a Med 400 fiber optic (0.4 millimeter diameter core) 1.8 meters in length and equiped with a stainless steel heat generating element having the configuration as shown in FIG. 4 and a length of about 9 millimeters, a diameter of about 1.0 millimeters, and a mass of about 0.1 grams. In air, a 68 watt Neodyminum-YAG laser manufactured by Messerschmidt of Munich, West Germany raised the temperature of the heat generating element from room temperature to about 500 degrees C. in about 0.5 seconds. Similarly, in air, a 6 watt Argon laser manufactured by Laser Ionics of Orlando, Fla. raised the temperature of the heat generating element to 654 degrees C. from a base line temperature of 25 degrees C. in five seconds. A two second burst from a 6 watt Argon laser raised the temperature of the heat generating element to 231 degrees from a base line temperature of 24 degrees C.

Measurements of laser intensity were made at the proximal end of the fiber optic by using a laser power meter Model 201 made by Coherent Radiation of Palo Alto, Calif. Temperature measurements of the element were made using a 30 gauge Model HPY-1 hypodermic thermocouple available from Omega Engineering of Stanford, Conn. and a digital temperature meter available from Analogic Corporation of Wakefield, Mass.

Tests were also made of the energy transfer by the device into liquid samples using both blood and tap water samples. Blood was withdrawn from several patients in a process which mixed approximately 7 milliliters of blood with 0.07 milliliters of 15 percent ethylene diamine tetraacetic acid (EDTA). The blood was pooled by mixing to obtain a uniform larger quantity. Conical polystyrene sample cups having a capacity of 2.0 milliliters were divided into two groups and filled respectively with 0.5 milliliters of tap water for 0.5 milliliters of blood.

The heat generating element was then immersed in the water or blood together with the thermocouple temperature probe. Tests were then made at 1 to 6 watts with an Argon laser for periods of 10 to 60 seconds to determine the heat generation of the device. Seven samples were tested for each combination of energy and time. The base line temperature for each test was 19-20 degrees C.

A 10 second burst of laser energy at 1 watt intensity raised the temperature of the water samples to an average of 33 degrees C. and the blood samples to an average of 46 degrees C. A 1 watt burst for 60 seconds raised the temperature of the water samples to an average of 52 degrees C. and blood to an average temperature of 66 degrees C.

Using a 6 watt Argon laser, a 10 second burst raised the temperature of the water samples to an average of 52 degrees C., and a 30 second burst raised the temperature of the water to an average of 87 degrees C., and a 60 second burst raised the temperature to an average of 98 degrees C. No tests were made with blood at a greater than 1 watt intensity.

Tests were also carried out to measure the effectiveness of the medical device on artery walls. A particularly surprising result of those experiments was the relative thermal insulation provided by an artery. It was found that a substantial temperature gradient existed across the wall of the artery when the device was used. This demonstrates that it is possible to remove an obstruction within an artery using the medical device of the present invention with a minimum amount of trauma to the surrounding tissue.

ANIMAL EXPERIMENT RESULTS

Bilateral cut-downs were performed on the femoral and carotid arteries of a male Shepherd-mix dog 82 pounds in weight. A Med 400 fiber having a stainless steel heat generating element mounted on the end as described above was inserted into the artery and positioned adjacent two of three sutures located in the right femoral artery to serve as markers. An Argon laser at a power level of 6 watts was used for 5-second bursts. The temperature increase of the artery and the heated element were measured in separate tests in the same artery. The thermocouple temperature probe located in the artery wall adjacent the heat generating element showed a temperature of 44 degrees C. after use of the laser from a base line temperature of 31.5 degrees C. In a second test the temperature of the heat generating element was measured after laser use at 66 degrees C. from a base line temperature of 34 degrees C.

Similar measurements were also made in the left femoral artery with the Argon laser at a power level of 6 watts, but using a two second burst. In the first test the temperature of the arterial wall increased from a base line temperature of 32 degrees C. to 36 degrees C. In the second test the temperature of the element within the artery increased from a base line temperature of 32.5 degrees C. to a final temperature of 47 degrees C. As can be seen, the artery has particularly good insulating qualities which protect the surrounding tissue.

Studies were also made of the effect of the heat generating element on the arterial wall itself. In these studies, the carotid arteries were exposed and for each artery three separate measurements were made at three different sites along the artery. For each measurement the temperature probe was located within the blood vessel to measure the temperature of the blood adjacent the heat generating element. Measurements of the outside diameter of the artery were made both before lasing and after lasing.

In the first set of tests, blood flow in the right carotid artery was stopped above and below the element by purse string sutures to simulate either a full occlusion by deposit or by the use of blood occlusion means such as a balloon. The results of those test are set forth below in Table I. The one second burst measurement is believed to be a result of a measurement error due to either a "spike" in the heat gain or malposition of the probe.

TABLE I

| Laser Duration (Secs) | Baseline Temp (°C.) | O.D. Of Vessel Pre-Lasing (mm) | Final Temp (°C.) | O.D. of Vessel Post-Lasing (mm) |
|---|---|---|---|---|
| 1 | 29 | 5.2 | 138 | 5.2 |
| 2 | 28 | 5.3 | 87 | 4.0 |
| 3 | 25 | 5.1 | 89 | 4.1 |

In a similar test, the left carotid artery was exposed and subjected to heating by the element. However, no purse string sutures were used to occlude the blood flow and the Argon laser was set at a power level of 6.4 watts. The results are set forth below in Table II.

TABLE II

| Laser Duration (Secs) | Baseline Temp (°C.) | O.D. Of Vessel Pre-Lasing (mm) | Final Temp (°C.) | O.D. of Vessel Post-Lasing (mm) |
|---|---|---|---|---|
| 1 | 38 | 5.0 | 38 | 5.1 |
| 2 | 37 | 5.0 | 36 | 5.0 |
| 3 | 38 | 4.8 | 40 | 4.9 |

As can be seen from the above studies of arteries in a dog, the heat generating element can be raised to a sufficient temperature to soften a deposit such as a fat without extensive damage to an artery. It has also been demonstrated that the insulation quality of arterial wall substantially reduces trauma to any adjacent tissue.

Because of its small relative diameter and size, the medical device can be used to cauterize bleeding or remove tissue in surgical procedures where there is little available space. One such procedure is surgery being conducted by means of an endoscope in a body cavity. The medical device can be directed along a channel defined by the endoscope until the heat generating element has been properly located in contact with the tissue. After the operator is satisfied that the element is properly and safely located, the element can be quickly heated. This provides safety since the heat energy is not conducted to the tissue until the operator can be certain that otherwise healthy tissue will not be damaged. Such use of the medical device of the present invention can be made in the treatment of a bleeding ulcer with the assistance of a gastrofiberscope.

The medical device embodying this invention can also be used to deliver localized heat within a lumen such as a blood vessel. The heat can be used to open a clot or soften and remove plaque and fatty deposits which are found in blood vessels. The heated element softens the deposit material so that the element may be pressed into and through the plaque to enlarge the channel in a constriction or create a channel through an obstruction. This produces a relatively smooth, uniform channel having a diameter which is controlled by the size of the heat generating element used. Clotting and regrowth of tissue is minimized by such a smooth, uniform channel. It is also possible to make a series of passes through the same obstruction or constriction to create an even larger channel.

What is claimed is:

1. A system for applying heat to a body site, the system comprising in operative association:
   (a) a medical device including an elongated light transmitting fiber having a proximal end and a distal end, and a heat generating element defining a cavity with vent means in flow communication with the cavity for permitting gas to escape from the cavity, the element having a selectively varying thickness and being mounted with respect to the distal end such that light transmitted by the fiber to the element is converted into heat by the element;
   (b) a light source associated with the proximal end of the fiber for providing sufficient light energy to raise the temperature of the element; and
   (c) temperature sensing means associated with the proximal end of the fiber for measuring the temperature of the element.

2. The system of claim 1 wherein the light source is a laser.

3. The system of claim 1 wherein the temperature sensing means is a pyrometer.

4. The system of claim 1 wherein the light source and temperature sensing means are associated with the proximal end of the fiber by beam splitting means.

5. The system of claim 1 including locking means for retaining the element on the fiber.

6. The system of claim 1 wherein the medical device includes an elongated tube carrying the fiber.

7. The system of claim 6 wherein the tube engages the heat generating element to help retain the element on the fiber.

8. The system of claim 6 wherein the fiber is slidably received in the tube.

9. The system of claim 6 wherein the tube carries blood flow occlusion means.

10. The system of claim 1 wherein the heat generating element is formed as a cylindrical member with a closed, rounded end having a selected thickness, and a side wall with a thickness less than the thickness of the end.

11. The system of claim 1 wherein the heat generating element includes a selectively located peripheral notch formed therein to limit the transfer of heat from the region distally of the notch to the region proximally thereof.

12. A localized heat applying medical device for applying heat to a site in a patient's lumen, the device comprising in operative association:
   an elongated light transmitting conduit having a proximal end and a distal end and a heat generating element defining a cavity with vent means therein for permitting gas to escape from the cavity, the element being mounted on the distal end such that light transmitted by the conduit to the element is converted by the element into heat to raise the temperature of the element and the element can then be contacted with material in the patient's lumen to alter the material; the conduit and heat generating element being adapted for insertion into the patient's lumen.

13. The medical device of claim 12 wherein the heat generating element is made of metal.

14. The medical device of claim 12 wherein the conduit is a light transmitting fiber.

15. The medical device of claim 14 wherein the distal end of the fiber is received in the cavity defined by the heat generating element.

16. The medical device of claim 15 wherein the inside surface of the cavity has been treated to increase its coefficient of emissivity.

17. The medical device of claim 12 wherein the exterior surface of the heat generating element is provided with a coating of poly(tetrafluoroethylene).

18. The medical device of claim 12 including locking means for retaining the heat generating element on the distal end of the conduit.

19. The medical device of claim 18 wherein the locking means includes an inwardly extending ridge on the element received in a groove defined by the light transmitting conduit.

20. The medical device of claim 12 wherein the heat generating element has a generally rounded exterior surface.

21. The medical device of claim 12 including an elongated tube having a proximal portion and a distal portion, the tube carrying the light transmitting conduit with the heat generating element beyond the distal portion of the tube.

22. The medical device of claim 21 wherein the tube defines a fluid passageway along its length.

23. The medical device of claim 22 further including centering means for positioning the conduit generally along the central axis of the tube.

24. The medical device of claim 21 including blood flow occlusion means carried by the tube adjacent the distal portion.

25. The medical device of claim 21 wherein the tube engages the element to help retain the element on the conduit.

26. The medical device of claim 21 wherein the light transmitting conduit is slidably carried by the tube.

27. The medical device of claim 12 wherein the light transmitting conduit is flexible.

28. The device of claim 12 wherein the heat generating element is elongated with a closed, rounded end having a selected thickness and a side wall with a thickness less than the thickness of the end.

29. The device of claim 28 wherein the heat generating element includes a peripheral notch formed therein to limit heat transfer from the region distally of the notch to the region proximally thereof.

30. A localized heat applying medical device for applying heat to a site, the device comprising in operative association:
(a) a flexible elongated light transmitting fiber having a proximal end and a distal end, the distal end adapted to emit light transmitted by the fiber;
(b) a metal heat generating element insertable into a lumen and defining a cavity into which the distal end of the fiber is positioned and a light receiving surface adapted to collect light emitted by the distal end of the fiber, the element converting the light into heat, the element having vent means in flow communication with the cavity for permitting gas to escape from the cavity; and
(c) means for mounted the element onto the distal end of the fiber such that light emitted by the distal end is received on the surface of the element, the mounting means including at least one inwardly extending peripheral ridge on the element which lockingly engages a corresponding groove defined by the fiber.

31. The medical device of claim 30 wherein the light receiving surface of the cavity has been treated to increase its coefficient of emissivity.

32. The medical device of claim 30 including an elongated tube having a proximal portion and a distal portion, the tube carrying the light transmitting fiber with the heat generating element beyond the distal portion of the tube.

33. The medical device of claim 32 including an inflatable balloon carried circumferentially about the tube adjacent the distal portion of the tube.

34. The medical device of claim 32 wherein the distal portion of the tube engages the heat generating element.

35. The medical device of claim 34 wherein the tube defines a fluid passageway along its length and the element defines at least one flute in fluid communication with the passageway and opening outside the element.

36. The medical device of claim 32 wherein the fiber is slidably received in the elongated tube.

37. The medical device of claim 36 wherein the tube includes three ridges extending into the fluid passageway and centering the conduit within the passageway.

38. The medical device of claim 31 further including an inflatable balloon carried circumferentially about the tube adjacent the distal protion of the tube, the interior of the balloon in fluid communication with a channel defined by one of the ridges.

39. The medical device of claim 30 wherein the heat generating element is elongated with a closed, rounded end having a selected thickness and a side wall with a thickness less than the thickness of the end.

40. The medical device of claim 39 wherein the heat generating element includes a peripheral notch formed therein to limit heat transfer from the region distally of the notch to the region proximally thereof.

41. A medical device for applying heat to a site in a patient's body, the device comprising in operative association;
(a) an elongated tube having a distal portion and defining a fluid passageway along its length;
(b) an elongated light transmitting fiber slidably carried by the tube in the passageway, the fiber having a proximal end and distal end; and
(c) a metal heat generating element mounted on the distal end of the fiber such that light transmitted through the fiber is converted by the element to heat, the element defining a cavity therein bounded in part by a closed, rounded end of a selected thickness and a sidewall of a thickness less than the thickness of the end, the element having vent means in flow communication with the cavity for permitting gas to escape from the cavity, the element being extendable beyond the distal portion of the tube.

42. medical device of claim 41 including an inflatable balloon carried circumferentially about the tube adjacent the distal portion of the tube.

43. The medical device of claim 41 wherein the element has a cross section greater than the cross section of the passageway defined by the tube.

44. The medical device of claim 41 including locking means for retaining the heat generating element on the distal end of the fiber.

45. The medical device of claim 41 wherein the distal end of the fiber is received in said cavity defined by the heat generating element.

46. The medical device of claim 45 wherein the inside surface of the cavity has been treated to increase its coefficient of emissivity.

47. The medical device of claim 41 wherein the exterior surface of the heat generating element is provided with a coating of poly(tetrafluoroethylene).

48. The medical device of claim 41 wherein the heat generating element includes a peripheral notch formed therein to limit heat transfer from the region distally of the notch to the region proximally thereof.

49. A method for removing at least a portion of material causing a constriction or obstruction in a lumen, the method comprising the steps of:
   (a) providing a medical device having a heat generating element mounted on the distal end of an elongated light transmitting fiber;
   (b) positioning the distal end of medical device within the lumen with the element in contact with the material;
   (c) transmitting light energy through the fiber such that the element becomes sufficiently hot to soften the material; and
   (d) moving the element into the material so as to form or enlarge a channel in the material.

50. The method of claim 49 including the step of introducing a liquid into the lumen before light transmission.

51. The method of claim 50 including the step of introducing a physiologically compatible gas into the lumen about the element after the liquid has been introduced but before light transmission.

52. The method of claim 51 including the step of occluding the lumen prior to introducing the liquid.

53. The method of claim 50 wherein the liquid is a radiopaque liquid.

54. The method of claim 49 including the step of introducing a gas into the lumen about the element prior to light transmission.

55. The method of claim 54 wherein the gas is carbon dioxide.

56. The method of claim 49 wherein the light transmission begins before the element is contacted with the material.

57. The method of claim 49 including producing the light energy to be transmitted with a laser.

58. The method of claim 49 including the additional step of measuring the temperature of element after light transmission.

59. The method of claim 58 wherein the temperature of the element is measured with a pyrometer.

* * * * *